United States Patent
Wakamatsu et al.

(10) Patent No.: US 8,352,198 B2
(45) Date of Patent: Jan. 8, 2013

(54) SENSING SENSOR AND CONCENTRATION MEASURING DEVICE

(75) Inventors: Shunichi Wakamatsu, Saitama (JP); Hiroyuki Kukita, Saitama (JP)

(73) Assignee: Nihon Dempa Kogyo Co., Ltd. (JP)

( * ) Notice: Subject to any disclaimer, the term of this patent is extended or adjusted under 35 U.S.C. 154(b) by 535 days.

(21) Appl. No.: 12/159,233

(22) PCT Filed: Dec. 12, 2006

(86) PCT No.: PCT/JP2006/326382
§ 371 (c)(1),
(2), (4) Date: Jun. 2, 2010

(87) PCT Pub. No.: WO2007/077967
PCT Pub. Date: Jul. 12, 2007

(65) Prior Publication Data
US 2010/0292935 A1    Nov. 18, 2010

(30) Foreign Application Priority Data

Dec. 28, 2005   (JP) .................... 2005-379295
Jul. 31, 2006   (JP) .................... 2006-209207

(51) Int. Cl.
*G01N 31/00* (2006.01)
*G01B 5/00* (2006.01)
(52) U.S. Cl. ............... 702/25; 702/31; 702/32; 702/33
(58) Field of Classification Search ............... 702/25, 702/27–35, 121–123, 179–189
See application file for complete search history.

(56) References Cited

FOREIGN PATENT DOCUMENTS
JP    2002-48797    *  2/2002
JP    2004-047929 A  *  2/2004

* cited by examiner

*Primary Examiner* — Phuong Huynh
(74) *Attorney, Agent, or Firm* — Andrus, Sceales, Starke & Sawall, LLP

(57) ABSTRACT

A user, when measuring a sensing target substance in fluid using a crystal sensor (sensing sensor) using a crystal vibrator whose natural frequency is varied by an absorption of the sending target, is able to easily and accurately grasp information peculiar to the crystal sensor, for instance, information regarding a quality thereof. An IC chip in which the information peculiar to the crystal sensor is stored is provided to the crystal sensor, and the peculiar information is read out at a side of a concentration measuring device when the crystal sensor is inserted into the concentration measuring device, and then displayed.

15 Claims, 8 Drawing Sheets

Fig.7

DISPLAY SCREEN

| MANURACTURER | ABC COMPANY |
|---|---|

| SERIAL NUMBER | 1 2 3 4 |
|---|---|

| DATE OF MANUFACTURE | ○(MONTH), ○(DATE), ○(YEAR) |
|---|---|

| SENSING TARGET | △△△ |
|---|---|

| STANDARD VALUE | ××mg/l |
|---|---|

CRYSTAL VIBRATOR INFORMATION

CUSTOMAER CODE

SELL-BY TERM

FREQUENCY DIFFERENCE : ○○○Hz

DETECTION CONCENTRATION : △△△mg/l

SENSING SENSOR AND CONCENTRATION MEASURING DEVICE

TECHNICAL FIELD

The present invention relates to a sensing sensor using a piezoelectric vibrator provided with an adsorbing layer for adsorbing a sensing target and electrodes, and whose natural frequency is varied by an absorption of the sensing target, and a concentration measuring device having the sensing sensor connected thereto and measuring a concentration of a substance in fluid based on an oscillation output from the sensing sensor.

BACKGROUND ART

In order to quantify the mass and concentration of a sensing target which is included in a very small amount in an environment or in a living body such as, for instance, an environmental pollutant like dioxin, PCB (polychlorinated biphenyl), and the like contained in a river, various antibiotics used for raising fishes and are remained in the blood of the raised fishes, and diseased substances such as prion which causes BSE (bovine spongiform encephalopathy) in an animal body tissue, there is known a sensing device using a crystal sensor being a sensing sensor provided with a crystal vibrator having, for instance, a crystal piece as a piezoelectric piece, in which an excitation electrode for exciting the crystal piece is respectively provided to one surface side and the other surface side of the crystal piece. Note that for the sensing target other than the above, a certain kind of protein in the blood, an antibody substance, a virus, a bacteria, or the like, can be cited.

This type of sensing device is composed of a crystal sensor, and a measuring device being electrically connected to the crystal sensor, and having an oscillation circuit, a frequency detecting section for detecting an oscillation output from the oscillation circuit, a display section for displaying a concentration of a sensing target, and the like. Further, at one surface side of the crystal vibrator, an absorbing layer having, for instance, an antibody adhered to the surface thereof is provided, in which the antibody is designed to selectively absorb one of the sensing target such as mentioned above, for instance, by an antigen-antibody reaction. Therefore, when the sensing target is absorbed in the absorbing layer, the frequency of the crystal piece varies in accordance with the absorption amount of the sensing target, so that by determining the variation amount, the concentration of the sensing target can be determined by using, for instance, a calibration curve.

Such a sensing device is disclosed in Patent Document 1, Patent Document 2, and the like, in which even a substance having a significant impact on the environment such as dioxin can be measured at ppt level. Specifically, a resonant frequency of the crystal vibrator is increased as the thickness of the crystal piece becomes thinner, and as the frequency becomes larger, the variation amount of the frequency with respect to the variation amount of the mass of a measuring substance is increased. In other words, as the crystal piece becomes thinner, a measurement sensitivity of the crystal sensor is improved, so that by making the crystal piece thin, it becomes possible to measure an infinitesimal amount of substance. Therefore, the sensing device is a simple device, not a large-scale one such as gas chromatography, and with the use of it, an analysis can be conducted in a short period of time, so that the sensing device is expected to be used broadly in the future.

However, this type of sensing device has problems as follows.

(1) In order to measure the sensing target with high accuracy, there is a need to strictly manage the quality of the antibody which forms the absorbing layer provided to the crystal vibrator, and in cases such that the antibody is an inferior product, a quality of the obtained antibody is deteriorated due to a bad management of atmosphere where the antibody is left, and a sell-by date is past, the antibody-antigen reaction does not proceed as expected, resulting that the measurement accuracy is lowered. Further, if assuming the crystal sensor is sold separately, the crystal sensor is necessary to be manufactured by a trusted manufacturer, and a quality thereof must be guaranteed. However, there is a possibility that a user cannot conduct an expected measurement especially when a pirated product with bad quality appears on the market.

(2) Further, since the kind of antibody being the absorbing layer used in the crystal sensor varies depending on the respective sensing targets, it is necessary to use the crystal sensor capable of being applied to the target to be measured, and if a crystal sensor different from that corresponding to the aimed target is used by mistake, a big trouble will occur such that the determination is reversed. However, in cases such that many kinds of sensing targets are continuously measured, there is a possibility of mistakenly using the crystal sensor. Furthermore, since it is impossible to determine whether or not the sensing sensor is used from its appearance, when assuming an aggravated case, a trader may obtain the used sensing sensor to thereby sell it to the user. When the used absorbing layer is applied, a measurement result with low measurement accuracy or an erroneous measurement result is generated, which results in an unexpected accident.

(3) Furthermore, although it is effective and necessary to examine which crystal sensor was used when studying the measurement results after the series of measuring operations are completed, to examine the correspondence between the measurement results and the crystal sensors is not always easy, and, for example, for a user conducting a large amount of analyses, the examination is a troublesome task.

(4) It often happens that the user needs to know information regarding the quality, and the like of the purchased crystal sensor in the beginning of its usage or after that, but, in such cases, the user has to read a package or instructions each time, and further to record the information. To manage while respectively pairing the crystal sensors with the packages, or the like is troublesome when the number of specimens is large, when there are many kinds of sensing targets, when the measurement is conducted in an outdoor environment, and the like, and there is a chance for causing an error. Especially at the time when the user needs to know information peculiar to a crystal sensor relating to a measurement which was conducted a long time ago, a lot of cases are conceivable in which the packages, or the like are already discarded.

Patent Document 1
Japanese Patent Application Laid-open No. 2001-083154 (FIG. 1)
Patent Document 2
Japanese Patent Application Laid-open No. Hei 11-183479 (Paragraph 0007, FIG. 1)

DISCLOSURE OF THE INVENTION

The present invention has been made under such circumstances, and an object thereof is to provide a sensing sensor which gives convenience to a user since information peculiar to the sensing sensor, for instance, information regarding a quality thereof can be grasped by the user easily with accuracy when measuring a sensing target substance in fluid using the sensing sensor, and a concentration measuring device connected to the sensing sensor.

A sensing sensor of the present invention having a piezoelectric to vibrator provided with an adsorbing layer for adsorbing a sensing target and electrodes, and whose natural frequency is varied by an absorption of the sensing target, and terminal portions electrically connected to the electrodes of the piezoelectric vibrator, the terminal portions being attachably/detachably connected to terminal portions at a side of a measuring device including an oscillation circuit for oscillating the piezoelectric vibrator, includes an information storing section for storing information peculiar to the sensing sensor which is deciphered by the measuring device. The sensing sensor is structured to be provided with a liquid accommodating portion to which a sample solution containing the sensing target, for instance, is supplied.

The information storing section is composed of, for instance, a memory provided on an integrated circuit element, a bar code read by an optical reading section at the side of the measuring device, a data storing section, or the like.

The peculiar information is information for guaranteeing a quality, for instance, and a concrete example thereof is information on a manufacturer, a serial number, a date of manufacture, a sell-by term, or the like. Further, the peculiar information may regard the sensing target sensed by the sensing sensor, and in this case, it is preferable to also include a concentration standard value of the sensing target. Furthermore, the peculiar information may be information indicating whether or not the sensing sensor is used, or information on a type of the absorbing layer.

A sensing device of the present invention being a concentration measuring device having the sensing sensor of the present invention, the oscillation circuit to which the sensing sensor is attachably/detachably connected via the terminal portions and oscillating the piezoelectric vibrator, and a measuring section for measuring a concentration of a sensing target in fluid based on an oscillation output from the oscillation circuit, includes a unit for deciphering information in the information storing section of the sensing sensor, and an information processing section for processing the deciphered information. This sensing device is provided with a display section for displaying the deciphered information, for instance. Further, the aforementioned concentration measuring device may be structured to include a unit for writing, after the sensing sensor is used, information indicating the used state in the information storing section of the sensing sensor. Further, the information processing section may be structured to include a unit for determining whether or not the sensing sensor is used based on the deciphered information, and notifying the used state.

In the present invention, the sensing sensor using the piezoelectric vibrator such as a crystal vibrator and being attachably/detachably connected to the concentration measuring device is structured to include the information storing section for storing information peculiar to the sensing sensor that is deciphered by the concentration measuring device, so that by connecting the sensing sensor to the concentration measuring device, the peculiar information is read out by the concentration measuring device, which provides convenience since it is possible to know what the sensing sensor is like easily and accurately. For the peculiar information, for instance, information regarding the quality, information regarding the sensing target, information regarding whether or not the sensing sensor is used, or the like, can be mentioned, and according to these pieces of information, the user can be protected, and the sensing sensor can be prevented from being mistakenly used at the time of the measurement.

BRIEF DESCRIPTION OF DRAWINGS

FIG. 7 is an explanatory view showing an example of a screen displayed on a display section of the sensing device;

BEST MODE FOR CARRYING OUT THE INVENTION (First Embodiment)

Figure 1:
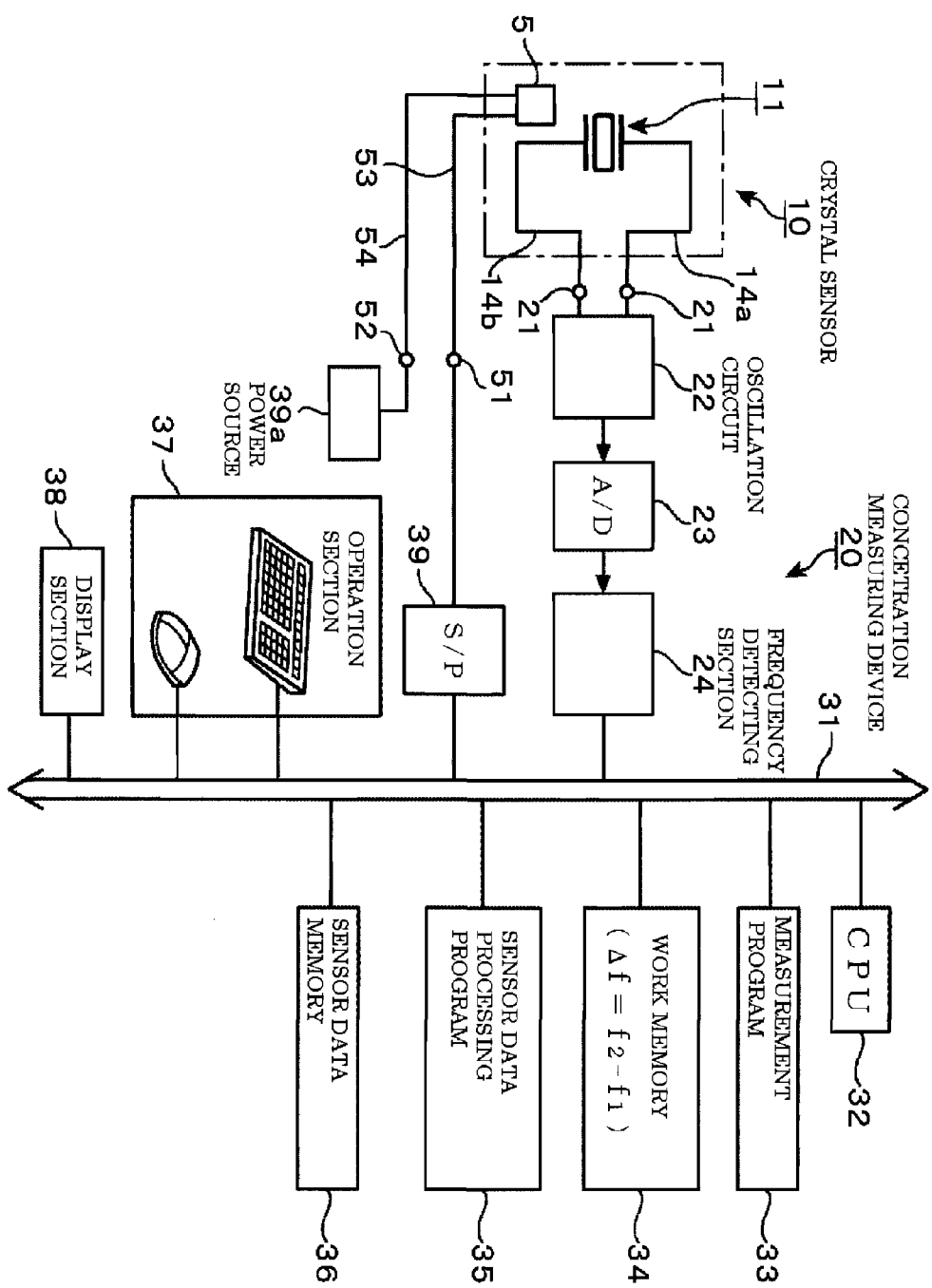
FIG. 1 is a whole structural diagram of a sensing device in which a crystal sensor and a concentration measuring device according to an embodiment of the present invention are combined.

FIG. 1 is a whole structural diagram of one embodiment of a sensing device including a concentration measuring device for measuring a concentration in fluid and a sensing sensor according to the present invention. A portion framed by a chain line 10 in FIG. 1 shows a crystal sensor being the sensing sensor, which is provided with a crystal vibrator (piezoelectric vibrator) 11 having a crystal piece as a piezoelectric piece, and an IC chip 5 being an integrated circuit element. "21" in FIG. 1 are terminal portions at a side of the measuring device to which electrodes of the crystal vibrator 11 are connected. "51" and "52" are respectively a terminal portion of a signal line and a terminal portion of a power supply line at the side of the measuring device connected to the IC chip 5. Note that the signal line and the power supply line are respectively simplified and displayed in one line. The crystal vibrator 11 is connected to an oscillation circuit 22 via the terminal portions 21. At a rear stage of the oscillation circuit 22, an A/D (analog/digital) converter 23 is provided, and at a rear stage of the A/D converter 23, a frequency detecting section 24 is provided. The frequency detecting section 24 is connected to a bus 31. Note that the respective sections located at stages behind the oscillation circuit 22 compose a measuring device (concentration measuring device in the present invention)

Next, an explanation will be made regarding respective sections composing one part of the concentration measuring device connected to the bus 31. "32" in the drawing is a CPU (central processing unit) being a calculating section, and "33" is a measurement program. This measurement program 33 is structured to execute a frequency difference detecting step for detecting a difference in oscillation frequency of the crystal vibrator 11 between when a solvent is put into the crystal sensor 10 and when a sample solution is put into the crystal sensor 10, and a step for calculating a concentration value of a sensing target calculated based on the frequency difference, or the like. "34" is a work memory being a region for performing a calculation to determine the concentration of the sensing target in the sample solution based on the frequency detected by the frequency detecting section 24, or the like.

"35" is a sensor data processing program for performing a processing by reading out data (sensor data) in the memory provided on the IC chip 5 of the crystal sensor 10. "36" is a sensor data memory formed of, for instance, a nonvolatile memory, and is a part for storing the sensor data. "38" is a display section which corresponds to, for instance, a monitor, and the like. "37" is an operation section formed of, for instance, a keyboard, a mouse, a screen displayed on the display section, and the like. "39" is a serial/parallel converter for converting serial data from the IC chip 5 into parallel data, and "39*a*" is a power supply section for supplying a voltage to the IC chip 5.

Figure 2:
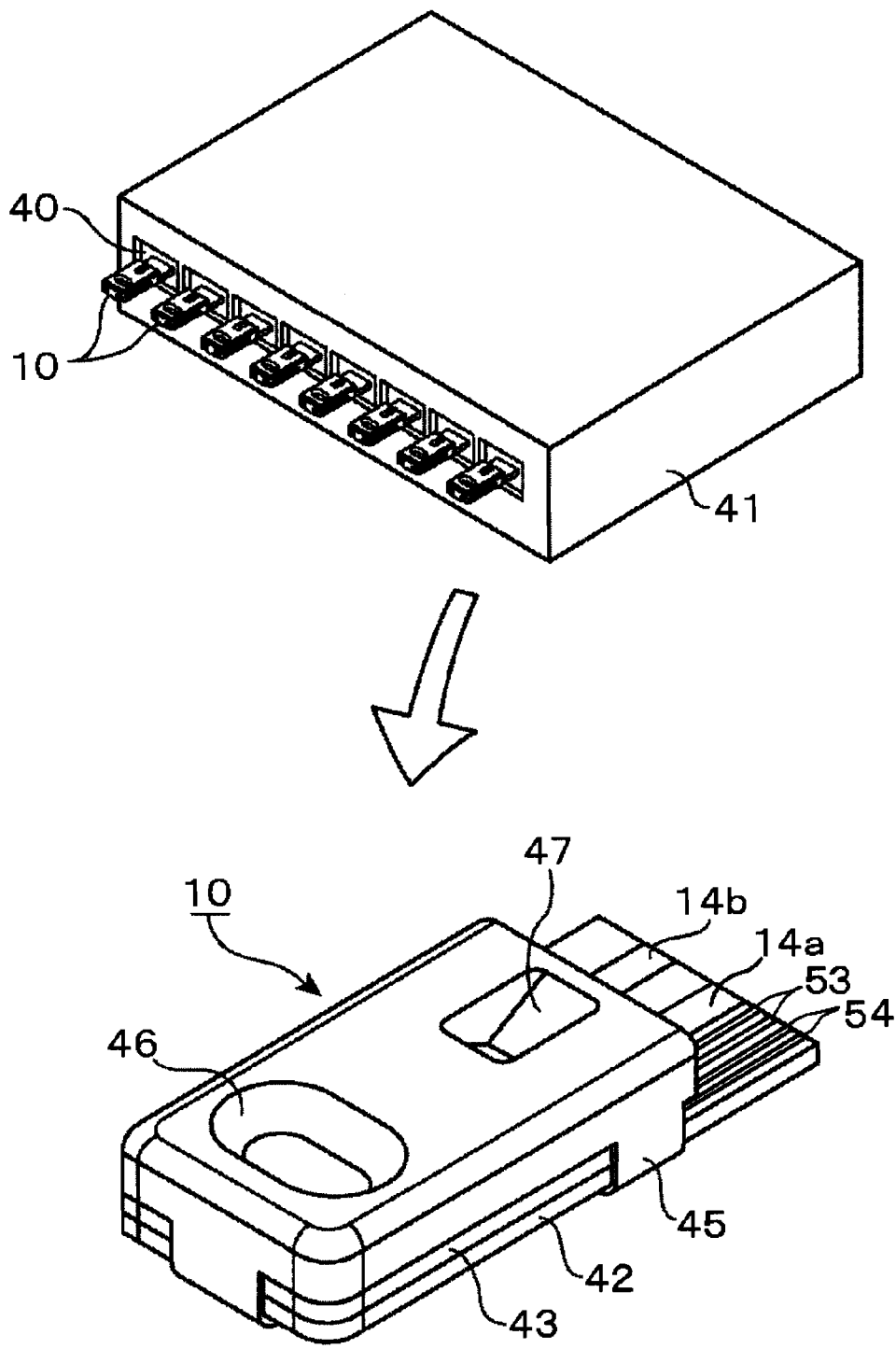
FIG. 2 is an example of the crystal sensor and a measuring device main body composing the sensing device.

FIG. 2 shows an example of a concrete structure of the respective sections composing the sensing device in FIG. 1. "41" in the drawing is a measuring device main body composing one part of the concentration measuring device, in which the oscillation circuit 22, the A/D converter 23 and the frequency detecting section 24 described in FIG. 1 are included. At a front surface of the measuring device main body 41, 8 insertion ports 40 are provided, and the crystal sensors 10 of 8 pieces at maximum are respectively attachably/detachably attached to these insertion ports 40. The terminal portions 21 shown in FIG. 1 are provided in the insertion port 40, and when the crystal sensor 10 is attached to the insertion port 40, the terminal portions 21 provided in the insertion port 40 are connected to later-described printed circuits 14*a* and 14*b* corresponding to terminal portions at a side of the crystal sensor 10, and at the same time, a printed circuit 53 and a printed circuit 54 each corresponding to a terminal portion of a signal line and a terminal portion of a power supply line of the IC chip 5 at the side of the crystal sensor 10 are respectively connected. Accordingly, the measuring device main body 41 and the crystal sensor 10 are electrically connected. This sensing device has an 8-channel structure, and when the crystal sensor 10 is electrically connected to the measuring device main body 41, as described above, the oscillation circuit 22 in FIG. 1 is prepared for 8 channels at maximum, and respective channel outputs are switched and thereby being output to the frequency detecting section 24 via the A/D converter 23.

Figure 3:
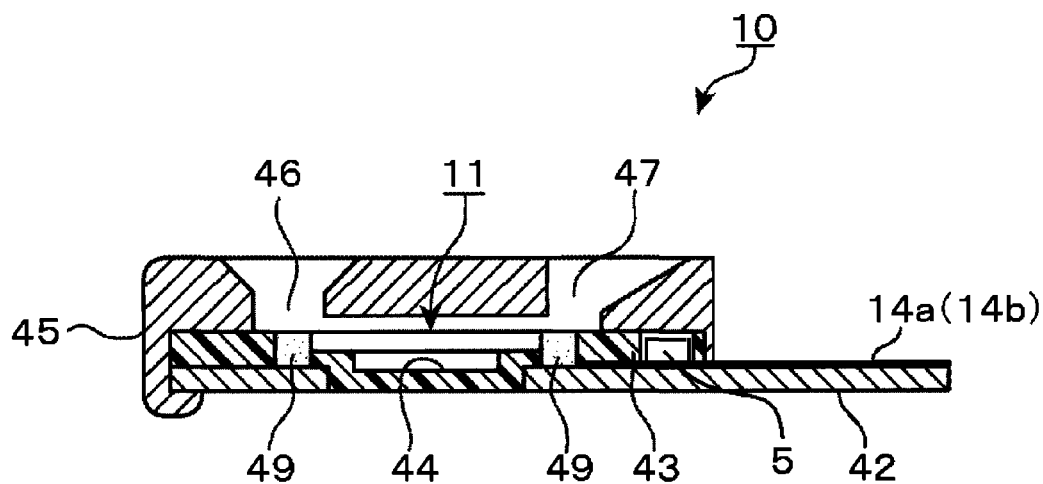
FIG. 3 is a vertical side view of the crystal sensor.
Figure 4:
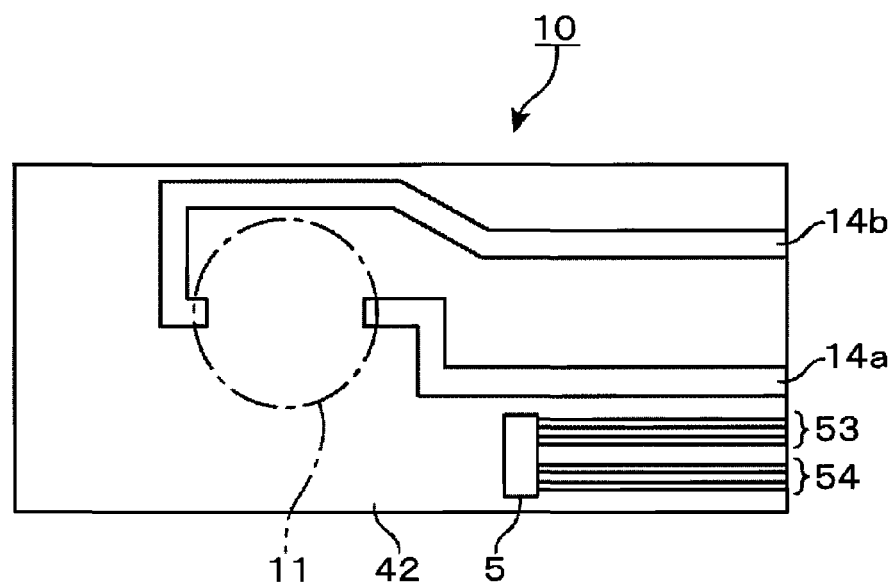
FIG. 4 is a plan view showing a printed-circuit board of the crystal sensor.

As shown in FIG. 2 to FIG. 4, the crystal sensor 10 is structured such that a rubber sheet 43 is formed over a wiring substrate such as, for instance, a printed-circuit board 42, the crystal vibrator 11 is provided so as to fill a recessed portion 44 formed on the rubber sheet 43, and a top cover case 45 is mounted over the rubber sheet 43. On the top cover case 45, there are formed a fill port 46 through which the sample solution being fluid to be measured is poured, and an observation port 47 for observing the sample solution, in which the sample solution is poured through the fill port 46, and a space at an upper surface side of the crystal vibrator 11 is filled with the sample solution (crystal piece is immersed into the sample solution). In the crystal sensor 10, a portion which is filled with the sample solution corresponds to a liquid accommodating portion. A lower surface side of the crystal vibrator 11 is made to be an air-tight space by the recessed portion 44, to thereby complete the formation of a Languban-typed crystal sensor.

Further, the IC chip 5 is mounted on the printed-circuit board 42, in which the mounting space of the IC chip 5 is formed by making a through hole in the rubber sheet 43 and by covering an upper portion of the through hole with the top cover case 45. Furthermore, on the printed-circuit board 42, the printed circuit 54 being the power supply line and the terminal portion of the IC chip 5 is simultaneously formed with the printed circuit 53 being the signal line and the terminal portion of the IC chip 5, as shown in FIG. 4.

Figure 5:
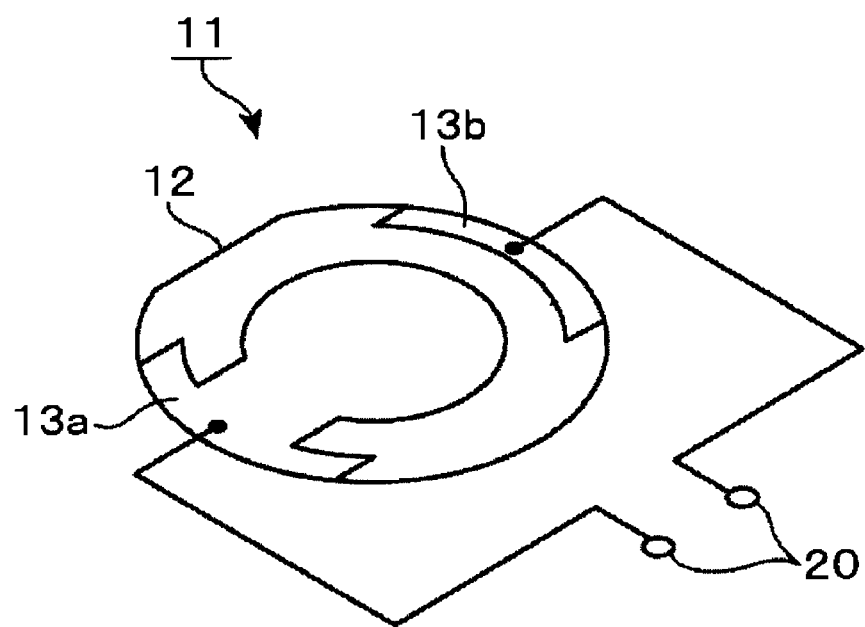
FIG. 5 is an explanatory view showing a crystal vibrator and wiring in the surrounding thereof which compose the crystal sensor.

As shown in FIG. 5, in the crystal vibrator 11, a crystal piece 12 of a circular shape, for instance, is provided at both surfaces thereof with respective electrodes 13*a* and 13*b* for oscillating the crystal piece 12, and each having the same shape, for instance (the electrode 13*b* on a rear surface side is formed serially with a peripheral edge on a front surface side). These electrodes 13*a* and 13*b* are respectively electrically connected to the printed circuits 14*a* and 14*b* provided on the printed-circuit board 42 via a conductive adhesive 49. Further, at one surface side of the crystal vibrator 11, for instance, at a surface of the circular-shaped portion of the electrode 13*a*, an absorbing layer (not shown) made of an antibody which captures the sensing target with the use of an antigen-antibody reaction is formed by, for instance, a coating.

Further, although being omitted in FIG. 2, to the measuring device main body 41, a computer, for instance, a personal computer is connected, and the measuring device main body 41 and the personal computer form the concentration measuring device. If explained by corresponding FIG. 1 and FIG. 2, the oscillation circuit 22, the analog/digital converter 23, the frequency detecting section 24 and the power supply 39*a* are provided in the measuring device main body 41, and the bus 31 and parts connected to the bus 31 are provided at the side of the personal computer.

Here, the explanation will be made regarding the data (sensor data) in the memory provided on the IC chip 5 of the crystal sensor 10. The memory provided on the IC chip 5 corresponds to an information storing section for storing information peculiar to the crystal sensor 10, in which the peculiar information is, for instance, information for guaranteeing the quality of the crystal sensor 10, for example, information on a manufacturer of the crystal sensor 10. In this embodiment, information on a serial number, a date of manufacture, and a sell-by term of the crystal sensor 10, being the peculiar information, is also stored in the memory. Note that the information on sell-by term also includes information on sell-by date. Further, for the peculiar information, information regarding the sensing target sensed by the crystal sensor 10, information corresponding to a concentration standard value of the sensing target, a type of the crystal vibrator 11, and the like, are included, and these data are also stored in the memory in this embodiment.

As the sensing target, there can be mentioned a substance that the absorbing layer provided to the crystal sensor 10 captures by the antigen-antibody reaction, such as dioxin, PCB, and prion, and in addition to that, a certain kind of protein, an antibody substance, a virus, a bacteria, or the like, can be mentioned. An example of the concentration standard value includes a tolerance concentration such as, for instance, a concentration of a contaminant in the water, in which the tolerance concentration is not limited to a value determined by the law, and may be a reference value, or the like, determined by a measurement institution, for instance.

Meanwhile, an explanation will be made regarding the sensor data processing program 35 provided to the concentration measuring device 20 (provided to the personal computer, in this example). This program 35 includes a step for reading out the data in the memory provided on the IC chip 5 and writing the data in the sensor data memory 36, a step for displaying the data and the processing results of the data on the display section 38, a step for determining whether or not the crystal sensor 10 has a guaranteed quality based on these data, and a step for determining, for instance, whether or not the manufacturer is a predetermined designated manufacturer, whether or not the sell-by term is past, and the like. By providing the step for determining whether or not the sell-by term is past, the use of a copy of the crystal sensor 10 is prevented. The program 35 corresponds to a unit for deciphering the data in the memory provided on the IC chip 5 (deciphering section) and a unit for processing the data. Further, it is allowable that data in the IC chip 5 is encoded.

This program 35 further includes a step for determining whether or not a measuring target substance input by an operator is a sensing target allocated to the crystal sensor 10, a step for determining, when the concentration of the sensing target is measured, whether or not the measurement value is within a standard value by comparing the measurement value with the concentration standard value, and the like. This program 35 still further includes a step for performing a processing for displaying the determination results of the respective steps and outputting a warning, in which, for instance, a processing for displaying on the screen and for outputting a warning sound, and the like, is conducted. Note that a display section formed of a liquid crystal may be provided to the measuring device main body 41.

Figure 6:
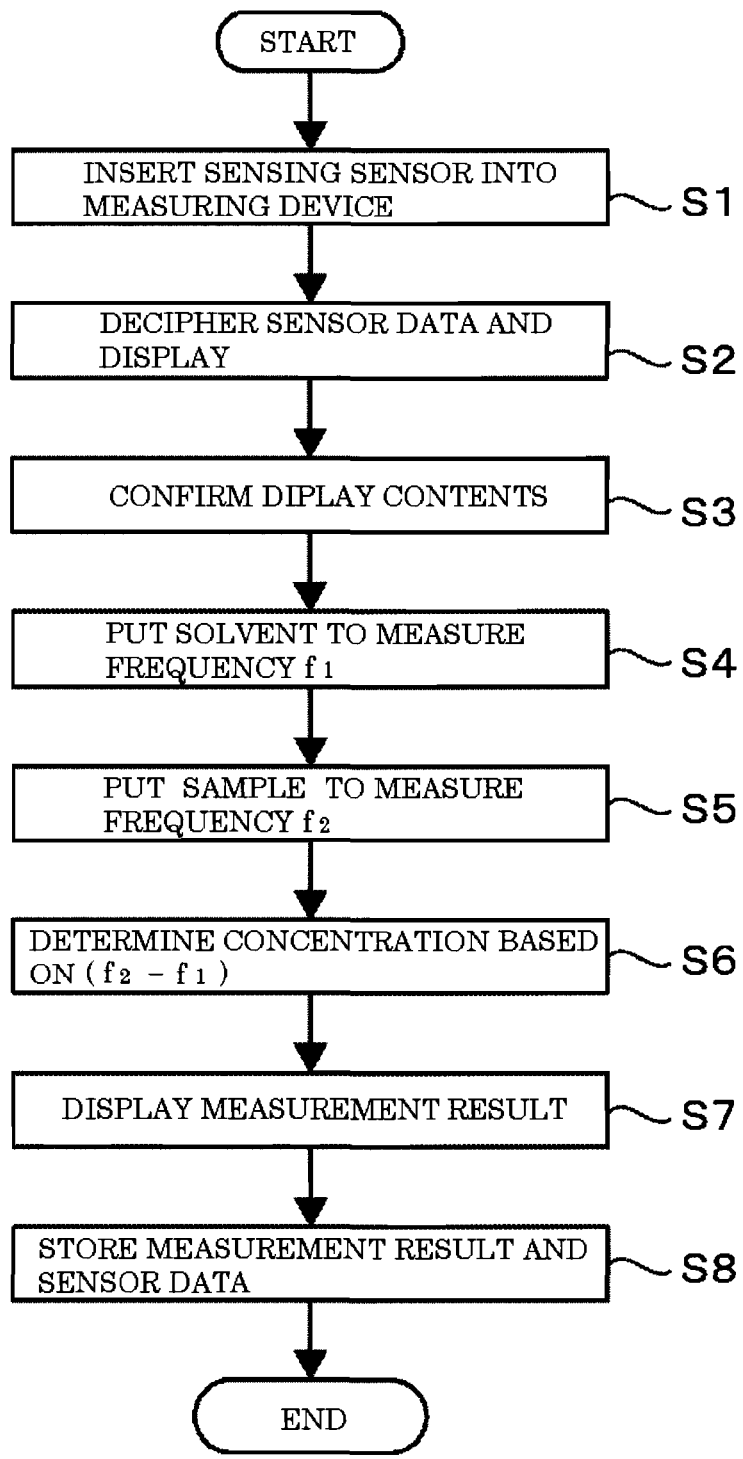
FIG. 6 is a flow chart showing a procedure for using the sensing device.

Next, an operation of thus structured sensing device will be explained. FIG. 6 is a flow chart for explaining the operation. First, the crystal sensor 10 is attached to the insertion port 40 of the measuring device main body 41 by an insertion (step S1). Accordingly, the crystal vibrator 11 of the crystal sensor 10 and the IC chip 5 are connected to the concentration measuring device 20, as described above. Note that 8 channels are prepared in this example, but, a case where 1 channel is used is described, for the sake of explanation. The sensor data stored in the memory on the IC chip 5 is read out by the sensor data program 35 of the concentration measuring device 20, and is displayed on the display section 38 (step S2). FIG. 7 is an example of a screen of the display section 38 on which the sensor data is displayed. This screen displays a manufacturer, a serial number, a date of manufacture, a sell-by term, a sensing target, a concentration standard value, crystal vibrator information and a customer code. The crystal vibrator information is information corresponding to the type of the crystal piece used in the crystal sensor 10, and a numerical value of the mass variation per a variation of 1 Hz, for instance, is included therein. Specifically, by obtaining the numerical value, the weight variation with respect to the frequency variation (absorption amount of sensing target) can be obtained. The customer code is a code allocated to a user to whom the crystal sensor 10 is delivered.

The operator confirms these display contents (step S3). For instance, by looking at the sell-by term, the operator determines whether or not the crystal sensor 10 is within the sell-by term, and confirms whether or not the sensing target coincides with a target to be measured.

Subsequently, to determine a blank value of the frequency of the crystal vibrator 11, only a predetermined amount of solvent, for instance, pure water is poured into one of the fill port 46 of the crystal sensor 10, to thereby immerse the crystal vibrator 11 in the pure water, and the crystal vibrator 11 is oscillated by the oscillation circuit 22. After a predetermined period of time is passed and the oscillation is stabilized, an oscillation output of the crystal vibrator 11 is input into the frequency detecting section 24, and the frequency detecting section 24 measures a frequency f1 oscillated by the crystal vibrator 11 (step S4).

Thereafter, a sample solution with which the concentration of the measuring target substance is examined, for instance, water in a river for measuring the concentration of dioxin, is poured into the fill port 46 of the crystal sensor 10 into which the pure water is already poured, to thereby immerse the crystal vibrator 11 into the sample solution. After a predetermined period of time is passed and the oscillation is stabilized, a frequency f2 oscillated by the crystal vibrator 11 is measured by the frequency detecting section 24 (step S5). The way of determining the frequency f2 is not limited to this example, and it may be such that the pure water is poured into the crystal sensor 10, and after the pure water in the crystal sensor 10 is discarded, the sample solution is subsequently put into the crystal sensor 10, and a value having the stabilized oscillation output is set as f2.

The measured frequencies f1 and f2 are respectively written in the work memory 34, and in the work memory 34, the frequency difference between f1 and f2 (f1−f2) is calculated by the measurement program 33. The mass of the sensing target absorbed in the absorbing layer is determined by multiplying the frequency difference by a constant, and since the absorption amount corresponds to the concentration of the sensing target in the sample solution, the value (f2−f1) corresponds to the concentration of the sensing target in the sample solution. Therefore, for instance, by previously forming a calibration curve for the respective sensing target and storing it in a separate memory, and also by providing a program for calculating the concentration of the sensing target based on the calibration curve, the concentration of the sensing target is determined when the value (f2−f1) is determined (step S6).

Thus determined concentration of the sensing target, for instance, dioxin, in the sample solution is displayed on the display section 38 together with the frequency difference value (f2−f1) (step S7). At this time, the operator compares the determined concentration with, for example, the standard value (tolerance concentration, in this case) of dioxin read out from the crystal sensor 10, to thereby determine whether or not the concentration is equal to or less than the tolerance concentration. Note that it is allowable that the determination can be automatically performed using the steps built in the program, and displayed accordingly. These pieces of information displayed on the display section 38, namely, the pieces of information peculiar to the crystal sensor 10 are stored in the memory by being corresponded to the measurement results (step S8), which can be taken out afterward.

Note that when conducting measurements by inserting the crystal sensors 10 into the respective 8 channels, each of the channels is switched, and data corresponding to the switched channel is displayed on the screen.

According to such an embodiment, when the crystal sensor 10 is attached to the concentration measuring device 20, the peculiar information is read out from the IC chip 5 of the crystal sensor 10, which provides convenience since it is possible to know what the sensing sensor is like easily and accurately. If the peculiar information is information regarding the quality such as, for instance, the manufacturer and the sell-by term, a user can confirm the quality, and since the management of the absorbing layer provided to the crystal sensor 10 affects the measurement accuracy, by confirming the quality, the measurement can be guaranteed to be performed accurately. Further, since the data in the IC chip 5 is hard to be read out, pirated products can be prevented from appearing on the market, which results in protecting the user since it is guaranteed that the user can use authentic products. From this point of view, the data is preferably encoded.

Further, by storing information on the sensing target of the crystal sensor 10 in the IC chip 5 as the peculiar information, the crystal sensor 10 can be prevented from being mistakenly used, and further, if the standard value of the sensing target is also included in the information, it is convenient at the time of the measurement. Furthermore, if it is designed such that such peculiar information is taken out from the crystal sensor 10 and stored at a side of the concentration measuring device 20 by being corresponded to the measurement result, even when there may be a problem in the quality of the crystal sensor 10, for instance, it is convenient for making a contact with a manufacturer at the time of analyzing and studying the measurement results afterward.

(Second Embodiment)

Another embodiment of the present invention will be explained. This embodiment is provided with a read/write function with respect to the memory (nonvolatile memory, in this case) in the IC chip 5 of the crystal sensor 10, in which the terminal portion 51 also includes a signal path for controlling the read/write operation. Further, the sensor data processing program 35 includes a program for writing, after the crystal sensor 10 is used, for instance, at the time when the measurement of the frequency f2 of the crystal sensor 10 is completed, information indicating the used state in the memory in the IC chip 5 of the crystal sensor 10, and a program for determining whether or not the crystal sensor 10 is used based on the information read out from the memory in the IC chip 5 of the crystal sensor 10, and displaying, if the crystal sensor 10 is used, the used state on the display section 38. Except these points, the second embodiment takes the same structure as in the first embodiment.

Figure 8:
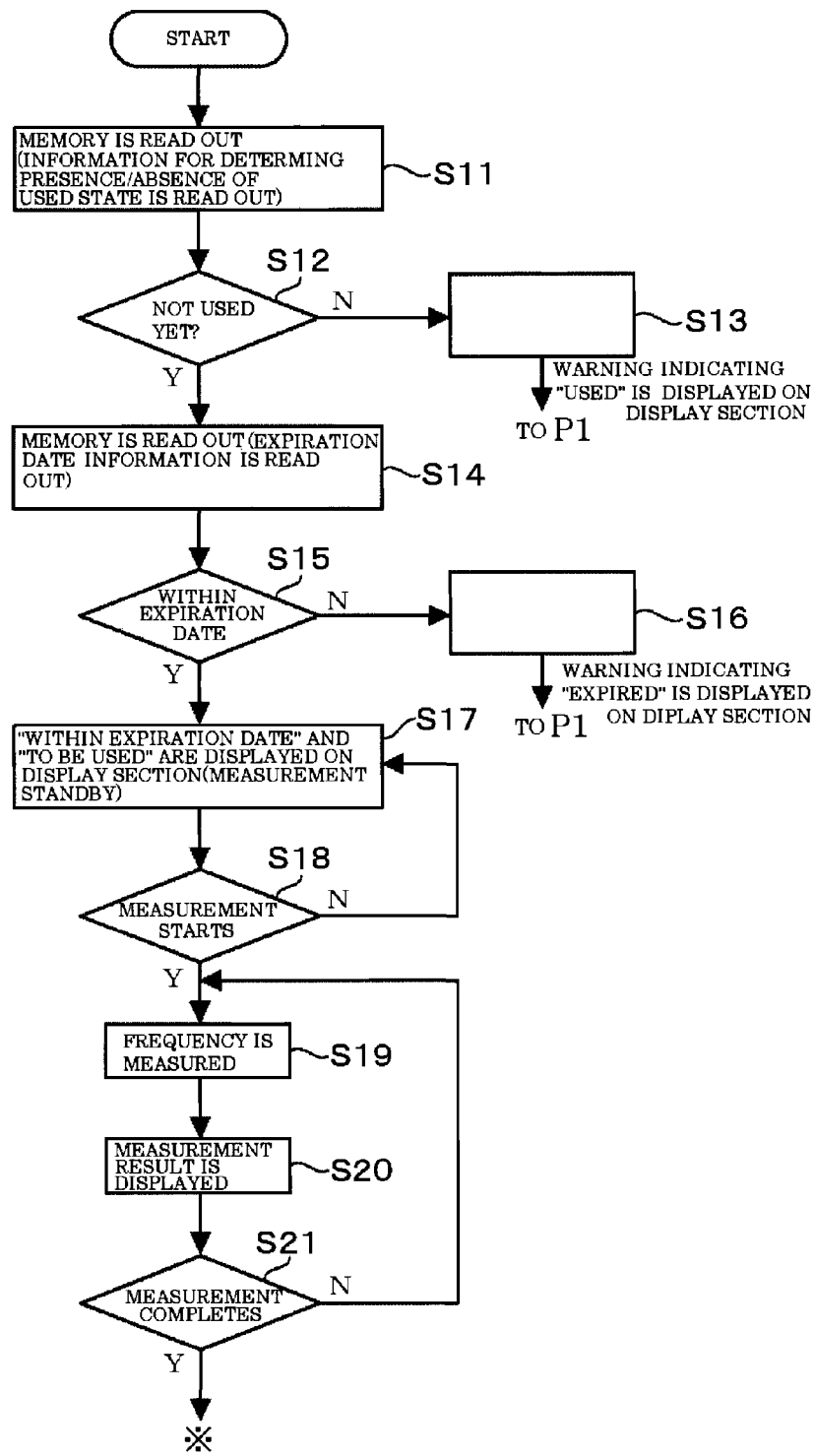
FIG. 8 is a flow chart showing a procedure for using a sensing device in another embodiment of the present invention.
Figure 9:
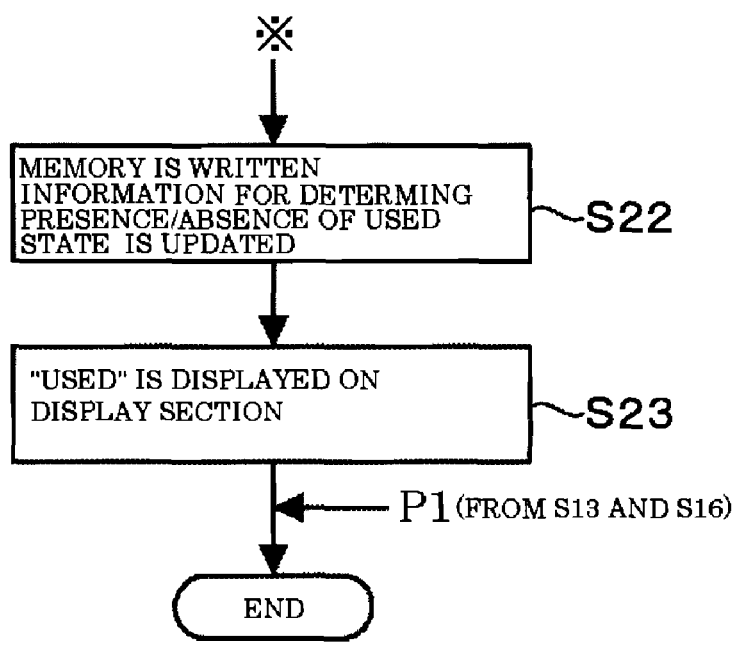
FIG. 9 is a flow chart showing the procedure for using the sensing device in the other embodiment of the present invention.

An operation of this embodiment will be described by referring to FIG. 8 and FIG. 9. First, the crystal sensor 10 is attached to the insertion port 40 of the measuring device main body 41 by an insertion. Subsequently, a power of the measuring device main body 41 is turned on, and a series of the following processing is conducted by the sensor data processing program 35 of the concentration measuring device 20. First, information for determining presence/absence of the used state is read out from the sensor data stored in the memory on the IC chip 5 (step 11), to thereby determine whether or not the crystal sensor 10 is used (step 12). If determined that the crystal sensor 10 is used, a warning indicating "used" is displayed on the display section 38 (step 13), and if determined it is not yet used, expiration date information (sell-by date) is read out from the sensor data stored in the memory on the IC chip 5 (step 14), to thereby determine whether or not the crystal sensor 10 is within the expiration date (step 15). If determined that the crystal sensor 10 is out of the expiration date, a warning indicating "expired" is displayed on the display section 38 (step 16), and if determined it is within the expiration date, the sensor data regarding, for instance, the manufacturer, the serial number, the date of manufacture, the sell-by term, the sensing target, the concentration standard value, the crystal vibrator information, the customer code, and the like of the crystal sensor 10, are displayed on the display section 38, as shown in FIG. 7 (step 17). Note that it is allowable that the type of the antibody being the aforementioned absorbing layer provided to the electrode 13 of the crystal sensor 10 is further written in the memory on the IC chip 5 as the peculiar information on the crystal sensor 10, and the information is read out from the memory and displayed on the display section 38.

Subsequently, after the operator confirms these display contents, the frequency of the sensing target is measured (step 18). The frequency measurement is conducted by the same operations as in the above-described step S4 to step S6 in the first embodiment (step 19), and thus obtained measurement result of the sensing target in the sample solution is displayed on the display section 38 (step 20). After the frequency measurement is completed (step 21), data indicating the used state is written in the memory on the IC chip 5 (step 22), and a warning indicating "used" is displayed on the display section 38 (step 23).

According to the above-described embodiment, after the frequency measurement is conducted using the crystal sensor 10 which is not yet used, the data indicating the used state is automatically written in the sensor data stored in the memory provided on the IC chip 5, and also the determination whether or not a crystal sensor which is about to be used is used is conducted, so that the possibility for performing the frequency measurement by mistakenly using the used crystal sensor is eliminated, which enables to protect the user, and to avoid the unexpected accident.

The present invention is not limited to be applied to the measurement of a substance in liquid as a substance in fluid, and it may be applied to a measurement of a toxic substance in the air such as sarin gas and hydrogen sulfide gas. Further, the information storing section is not limited to the IC chip, and it may be a bar code. In this case, an optical reader for reading the bar code is provided to the insertion port 40 at the side of the measuring device main body 41, and the bar code indicating the peculiar information is provided on the printed-circuit board 42 of the crystal sensor 10 at a position corresponding to the optical reader when the crystal sensor 10 is inserted into the insertion port 40 at the side of the measuring device main body 41. Furthermore, the information storing section may be magnetic data such as used in a cash card of a bank, which is structured such that, for example, the magnetic data is provided on a surface of the printed-circuit board 42 of the crystal sensor 10, and the magnetic data is read out by the measuring device main body 41 when the crystal sensor 10 is inserted into the insertion port 40 at the side of the measuring device main body 41.

The invention claimed is:

1. A sensing sensor being attachably/detachably connected to a main body of a measuring device for sensing a sensing target based on variation of natural frequency of a piezoelectric vibrator, comprising:

a wiring substrate;

a piezoelectric vibrator being provided on the wiring substrate parallel therewith and having respective electrodes being formed on both surfaces of a piezoelectric piece, wherein the electrode of another surface side of the piezoelectric piece being faced to a recessed portion divided from a space for filling the sample solution;

an absorbing layer being formed on one surface side as an upper surface of a piezoelectric piece for capturing the sensing target in a sample solution;

an information storing section provided at the wiring substrate for storing information peculiar to said sensing sensor which is deciphered by the measuring device;

a cover case surrounding an upper space over the one surface side of the piezoelectric piece for forming a space to fill the sample solution and having a fill port through which the fluid sample solution is poured;

wherein said terminal portions are connected to terminal portions comprising a unit for determining whether or not said sensing sensor is used based on the deciphered information, and indicating the used state.

2. The sensing sensor according to claim 1, wherein said information storing section comprises a memory provided on an integrated circuit element.

3. The sensing sensor according to claim 1, wherein said information storing section comprises a bar code read by an optical reading section at the side of the measuring device.

4. The sensing sensor according to claim 1,
wherein said information storing section comprises a magnetic data storing section.

5. The sensing sensor according to claim 1,
wherein the peculiar information comprises information for guaranteeing a quality.

6. The sensing sensor according to claim 5,
wherein the peculiar information comprises a manufacturer.

7. The sensing sensor according to claim 5,
wherein the peculiar information comprises either a serial number, a date of manufacture, or a sell-by term.

8. The sensing sensor according to claim 1,
wherein the peculiar information comprises the sensing target sensed by said sensing sensor.

9. The sensing sensor according to claim 8,
wherein the peculiar information comprises a concentration standard value of the sensing target.

10. The sensing sensor according to claim 1,
wherein the peculiar information comprises information indicating whether or not said sensing sensor is used.

11. The sensing sensor according to claim 1,
wherein the peculiar information comprises a type of the absorbing layer.

12. A concentration measuring device, comprising:
a sensing sensor according to claim 1;
an oscillation circuit for oscillating the piezoelectric vibrator;
a measuring section for measuring a concentration of a sensing target in fluid based on an oscillation output from the oscillation circuit;
an output section for an output of a result of measurement measured by the measuring section;
a unit for deciphering information in said information storing section of said sensing sensor; and
an information processing section for processing the deciphered information.

13. The concentration measuring device according to claim 12, further comprising
a display section for displaying the deciphered information.

14. The concentration measuring device according to claim 12, further comprising
a unit for writing, after said sensing sensor is used, information indicating a used state in said information storing section of said sensing sensor.

15. The concentration measuring device according to claim 12, further comprising
a unit for determining whether or not said sensing sensor is used based on the deciphered information, and indicating the used state.

* * * * *

UNITED STATES PATENT AND TRADEMARK OFFICE
CERTIFICATE OF CORRECTION

PATENT NO.       : 8,352,198 B2
APPLICATION NO.  : 12/159233
DATED            : January 8, 2013
INVENTOR(S)      : Shunichi Wakamatsu et al.

It is certified that error appears in the above-identified patent and that said Letters Patent is hereby corrected as shown below:

Title Page:

The filing date of International Patent Application No. PCT/JP2006/326382 should be listed as follows:
  (22) PCT Filed: December 27, 2006

Signed and Sealed this
Twenty-eighth Day of May, 2013

Teresa Stanek Rea
*Acting Director of the United States Patent and Trademark Office*